(12) United States Patent
Paul et al.

(10) Patent No.: US 10,500,294 B2
(45) Date of Patent: Dec. 10, 2019

(54) APPARATUS FOR THE DISINFECTION OF MEDICAL INSTRUMENTS

(71) Applicant: Trividia Health, Inc., Fort Lauderdale, FL (US)

(72) Inventors: Patrick J. Paul, Boca Raton, FL (US); Edward David Arguello, Weston, FL (US); Brent E. Modzelewski, Boca Raton, FL (US)

(73) Assignee: Trividia Health, Inc., Fort Lauderdale, FL (US)

( * ) Notice: Subject to any disclaimer, the term of this patent is extended or adjusted under 35 U.S.C. 154(b) by 0 days.

(21) Appl. No.: 14/814,434

(22) Filed: Jul. 30, 2015

(65) Prior Publication Data

US 2016/0030613 A1    Feb. 4, 2016

Related U.S. Application Data

(60) Provisional application No. 62/031,074, filed on Jul. 30, 2014.

(51) Int. Cl.
*A61L 2/10* (2006.01)
*A61L 2/00* (2006.01)

(52) U.S. Cl.
CPC ............ *A61L 2/10* (2013.01); *A61L 2202/24* (2013.01)

(58) Field of Classification Search
CPC ........................................... A61L 2/10
USPC ........................................... 422/24
See application file for complete search history.

(56) References Cited

U.S. PATENT DOCUMENTS

| 7,843,328 | B2 | 11/2010 | Redmond et al. | |
| 8,431,074 | B2 | 4/2013 | Neer | |
| 2005/0101854 | A1 | 5/2005 | Larson et al. | |
| 2006/0245131 | A1* | 11/2006 | Ramey | H02J 7/0029 361/90 |
| 2006/0261781 | A1* | 11/2006 | Oberding | H02J 7/0044 320/132 |
| 2011/0213339 | A1 | 9/2011 | Bak | |
| 2012/0100601 | A1* | 4/2012 | Simmons | A61B 5/14532 435/287.7 |
| 2013/0294969 | A1* | 11/2013 | Chen | A61L 2/10 422/28 |

(Continued)

FOREIGN PATENT DOCUMENTS

KR    2015016694 A  *  2/2016

OTHER PUBLICATIONS

English machine translation of Doc. No. KR 2015016694 A provided by KIPO: "The multifunctional stand for the ear thermometer," 2015, Yang et al.*

*Primary Examiner* — Kevin Joyner
*Assistant Examiner* — Holly M Mull
(74) *Attorney, Agent, or Firm* — Greenberg Traurig, LLP; David J. Dykeman; Roman Fayerberg

(57) ABSTRACT

Devices, methods and systems of disinfecting medical instruments, more particularly blood glucose meters. A disinfection cradle including a flat base for positioning the cradle on a surface, the cradle having a receptacle configured to receive the diagnostic apparatus, and a UV source positioned in the receptacle that is configured to administer a disinfection cycle to the diagnostic apparatus by directing UV light outward at the diagnostic apparatus received in the receptacle, the UV light being able to act as a disinfecting agent to the disinfection cradle and diagnostic apparatus.

7 Claims, 6 Drawing Sheets

(56) References Cited

U.S. PATENT DOCUMENTS

2013/0323120 A1    12/2013  Ma
2014/0166900 A1*   6/2014   Nelson .................. A61L 2/10
                                                   250/455.11
2015/0313354 A1*   11/2015  Mongan ................ A46B 17/06
                                                   15/22.1

* cited by examiner

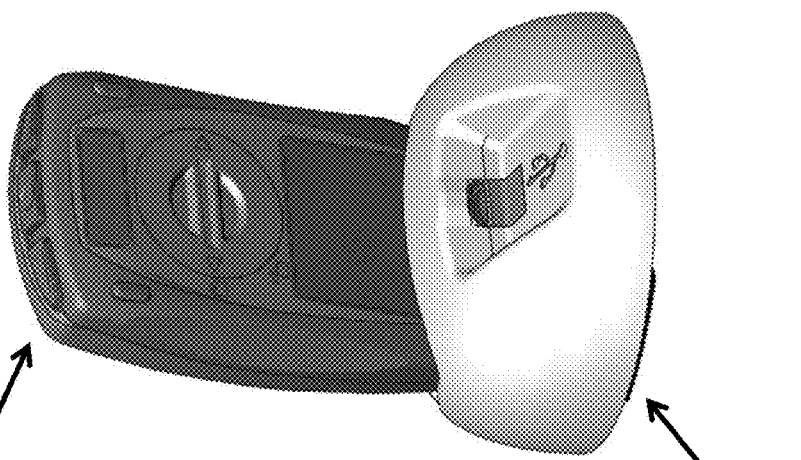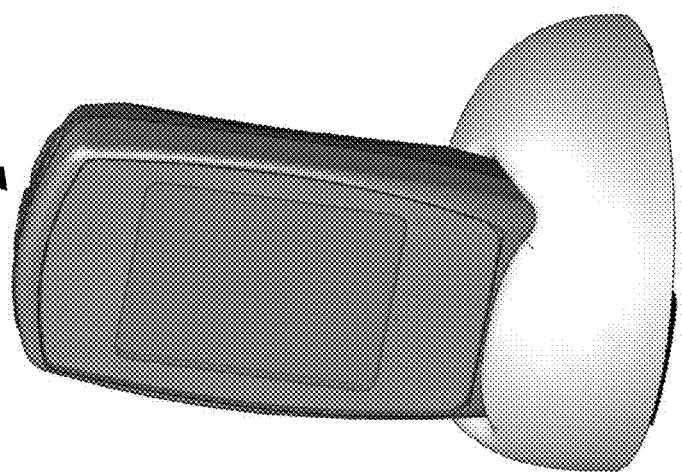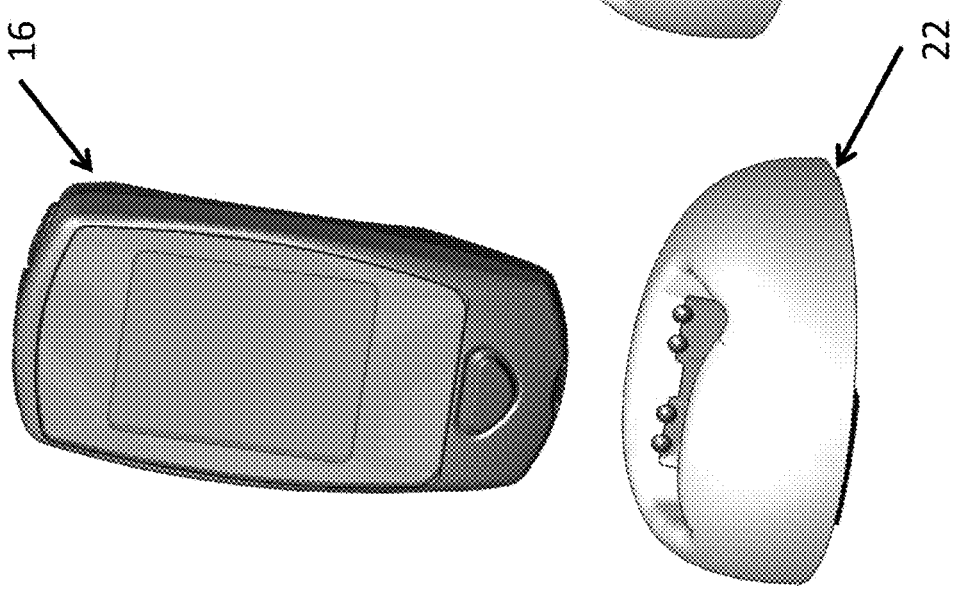

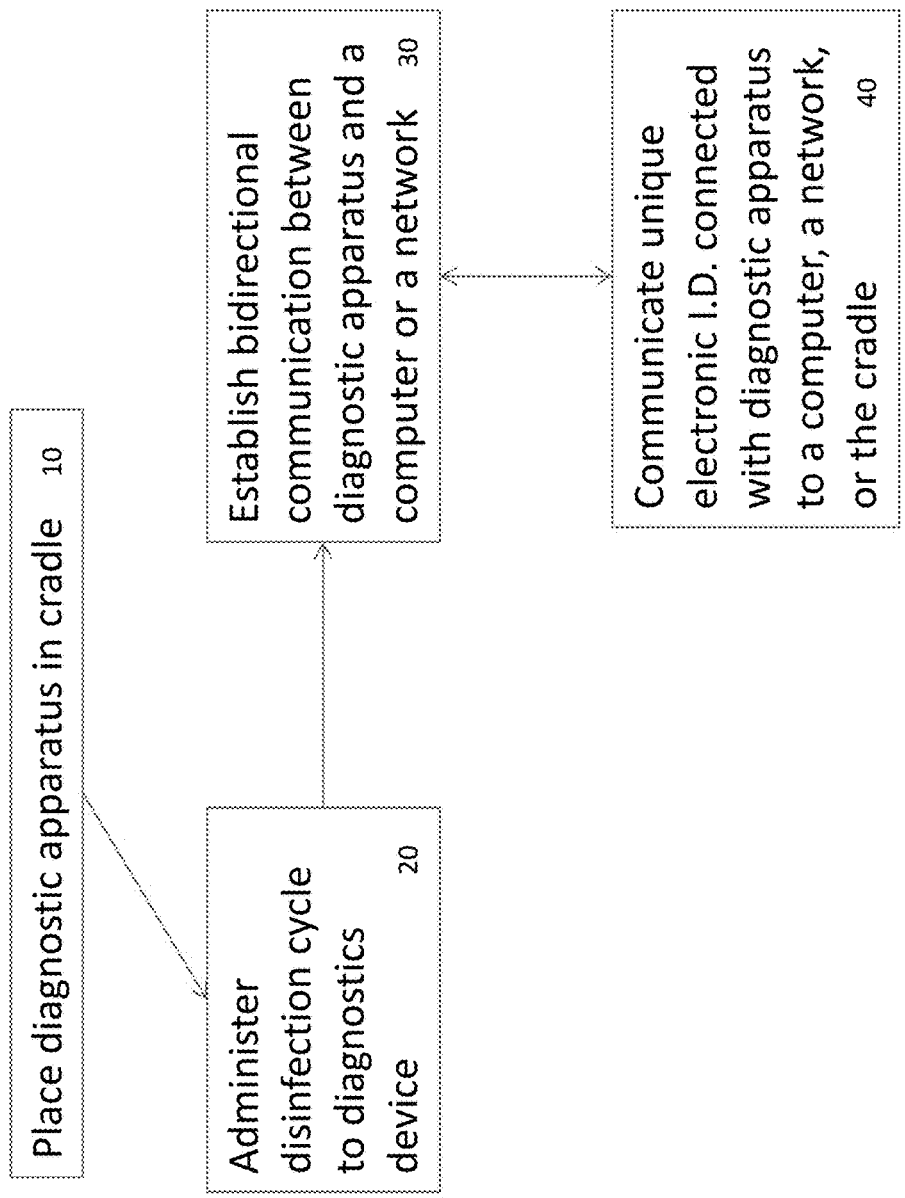

APPARATUS FOR THE DISINFECTION OF MEDICAL INSTRUMENTS

RELATED APPLICATIONS

This application claims the benefit of and priority to U.S. Provisional Application Ser. No. 62/031,074, filed Jul. 30, 2014, the entirety of which is hereby incorporated herein by reference.

BACKGROUND

1. Field

The present disclosure is directed to an apparatus for the disinfection of medical instruments, particularly the disinfection of blood glucose meters, utilizing ultraviolet Wavelength (UV) light.

2. Background

Blood glucose meters (BGMs) have been widely used since the 1980s for determining the approximate concentration of glucose in the blood. Medical personnel often share glucometers to test the blood glucose level of multiple patients.

The use of glucometers with multiple patients has caused cross-contamination concerns. The transmittal of dangerous bacteria, viruses and funguses can have very serious consequences for patients and medical personnel, for example the transmittal of Hepatitis and HIV viruses can cause death.

In early 2014 the FDA issued guideline documents to address this cross-contamination problem. Most BGM manufacturers have incorporated into their Instructions for Use (IFU) procedures related to cleaning and disinfecting the BGMs, and specific cleaning and disinfecting agents for which the effectiveness of the procedures has been validated.

Cleaning agents typically contain fairly aggressive chemical compounds (bleach, oxygen peroxide, ammonium chloride salts among others) and they can have adverse effects on the BGM housing and labeling. Additionally, the cleaning solution can penetrate the BGM (for example via the strip port) and cause internal corrosion of the BGM's electronics which could lead to faulty or defective devices. Further, the cleaning and disinfection of BGMs is also difficult, time consuming and entirely operator-dependent.

It would be advantageous to have an effective system for supplementing the cleaning and disinfection of BGMs that can minimize cross-contamination problems, improve disinfection efficiency, success rate, safety and consistency while not requiring additional human intervention. It would be further advantageous if the cleaning and disinfection of BGMs is less difficult, time consuming and not entirely operator-dependent.

SUMMARY

The present disclosure is directed to an apparatus for the disinfection of medical instruments, particularly the disinfection of blood glucose meters. In particular, some embodiments relate to a disinfection cradle comprises a flat base for positioning the cradle on a surface, with a receptacle substantially on top of the cradle that is configured to receive a diagnostic apparatus. The cradle can have one or more ports enabling the cradle to communicate with the diagnostic apparatus, and one or more ports enabling the cradle to establish communication between the diagnostic apparatus and a computer or a network. The base of the cradle is equipped with a source of ultraviolet light, such as LEDs (UV LEDs) that holds a diagnostic apparatus, which in some embodiments may be a Blood Glucose Meter (BGM). The UV LEDs direct UV light outward at the diagnostic apparatus to administer a disinfection cycle to the diagnostic apparatus. In some embodiments the receptacle contains electrical contacts which provide power to the diagnostic apparatus and which may allow for recharging of the diagnostic apparatus. In some embodiments the diagnostic apparatus includes a UV LED source approximate at least one test strip port. In some embodiments the UV LEDs in the cradle act as a disinfecting agent for the cradle and the diagnostic apparatus.

In some embodiments, the cradle further comprises a counter. The counter maintains a cumulative count of disinfection cycles performed on the diagnostic apparatus and generates a disinfection history for the diagnostic apparatus.

In some embodiments the communication between the diagnostic apparatus and the computer or the network is bidirectional communication. In some embodiments the computer or the network is part of a health care establishment, such that the bidirectional communication allows the health care establishment to generate and monitor a record of the disinfection history of the diagnostic apparatus.

In some embodiments the cradle further comprises a tracking function configured to monitor the disinfection cycle and to indicate the degree of completion of the disinfection cycle. In some embodiments the tracking function is a timer.

In some embodiments the diagnostic apparatus includes a lock out function. The lock out function is configured to prevent the diagnostic apparatus from functioning until the cradle has administered the disinfection cycle to the diagnostic apparatus.

In some embodiments, there is disclosed a disinfection cradle comprising an enclosure or chamber containing a cradle, wherein the chamber or enclosure can be closed with a door or cover, with a flat base for positioning the enclosure or chamber on a surface. The cradle has a receptacle located substantially on top of the cradle and configured to receive a diagnostic apparatus, the cradle having one or more ports enabling the cradle to communicate with the diagnostic apparatus, and one or more ports enabling the cradle to establish communication between the diagnostic apparatus and a computer or a network. The base of the cradle is equipped with ultraviolet LEDs (UV LEDs) that holds a diagnostic apparatus, which in some embodiments may be a Blood Glucose Meter (BGM). The UV LEDs direct UV light outward at the diagnostic apparatus to administer a disinfection cycle to the diagnostic apparatus. In some embodiments the diagnostic apparatus includes a UV LED source approximate at least one test strip port.

In some embodiments, the communication between the diagnostic apparatus and the computer or the network is bidirectional communication. In some embodiments the computer or the network is part of a health care establishment, such that the bidirectional communication allows the health care establishment to generate and monitor a record of the disinfection history of the diagnostic apparatus.

In some embodiments, there is disclosed a method for disinfecting a diagnostic apparatus comprising placing the diagnostic apparatus in a cradle, and administering a disinfection cycle to the diagnostic apparatus by delivering a controlled UV dose to a target area on the diagnostic apparatus. The cradle comprises a flat base for positioning the cradle on a surface, with a receptacle substantially on top of the cradle that is configured to receive the diagnostic apparatus. The cradle has one or more ports enabling the cradle to communicate with the diagnostic apparatus, and one or more ports enabling the cradle to establish communication between the diagnostic apparatus and a computer or a network. The base of the cradle is equipped with ultraviolet LEDs (UV LEDs) that holds a diagnostic apparatus, which in some embodiments may be a Blood Glucose Meter (BGM). The UV LEDs direct UV light outward at the diagnostic apparatus to administer the disinfection cycle to the diagnostic apparatus. In some embodiments the controlled dose is a dose of UV light from about 1 mJ/cm$^2$ to about 200 mJ/cm$^2$.

In some embodiments, the communication with the computer or the network is bidirectional communication. In some embodiments the method further comprises, after the delivering step, establishing the bidirectional communication between the diagnostic apparatus and a computer or a network, wherein the computer or the network is part of a health care establishment such that the bidirectional communication allows the health care establishment to generate and monitor a record of a disinfection history of the diagnostic apparatus. In some embodiments, the cradle further comprises a unique electronic I.D. that may be communicated to the diagnostics apparatus and/or the computer or the network that is connected to the diagnostics apparatus.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 1 illustrates a front view of a disinfective cradle and a blood glucose meter not inserted into the disinfective cradle, according to some embodiments;

FIG. 2 illustrates a front view of a disinfective cradle and a blood glucose meter inserted into the disinfective cradle, according to some embodiments;

FIG. 3 illustrates a rear view of a disinfective cradle and a blood glucose meter inserted into the disinfective cradle, according to some embodiments;

FIG. 8 is a flow chart illustrating an embodiment of a new method for disinfecting a diagnostic apparatus.

Figure 4:
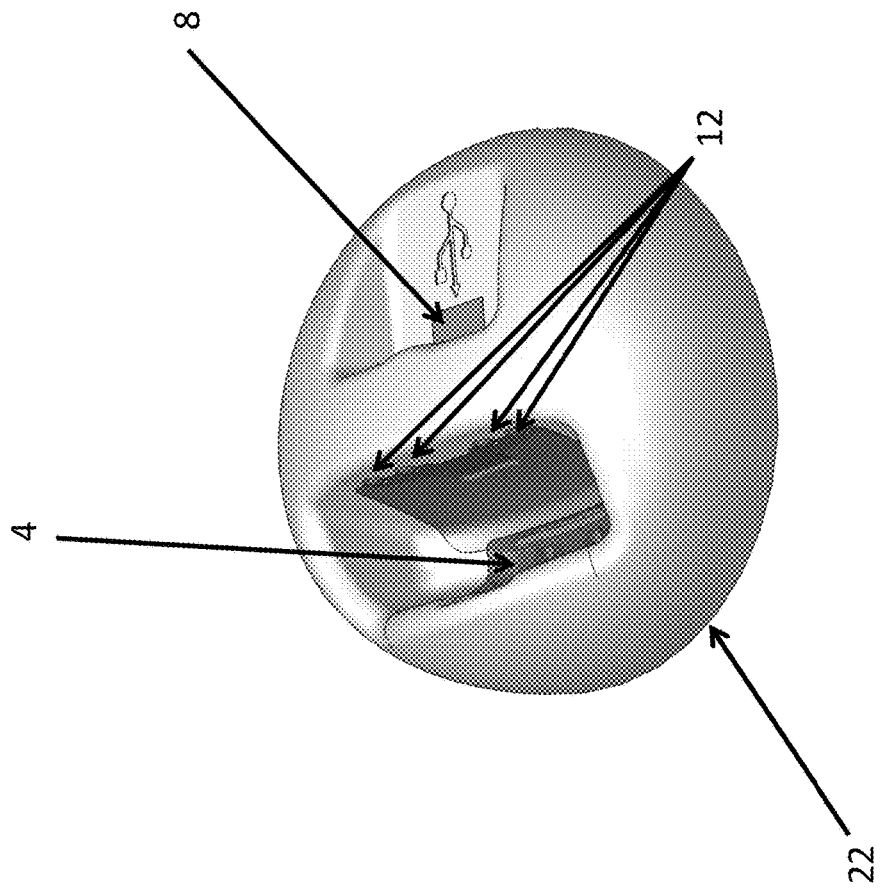
FIG. 4 is a perspective view of a disinfective cradle, according to some embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The present disclosure is directed to an apparatus for the disinfection of medical instruments, particularly the disinfection of blood glucose meters (BGMs), utilizing ultraviolet Wavelength (UV) light. In particular, some embodiment relate to a disinfection cradle equipped with ultraviolet LEDs (UV LEDs) (or like light sources) that holds one (or more) BGM and that administers a disinfection cycle to the BGM through delivery of a controlled dose of ultraviolet light (controlled UV dose) from the UV LEDs to the BGM (or more than one BGM). The controlled UV dose depends on the UV intensity (as may be measured by UV sensors), the flow rate, and the UV transmittance (UVT). In some embodiments the UV LEDs may deliver a controlled UV dose of from 1 to 200 mJ/cm$^2$. For specific disinfection of bacteria, the controlled UV dose should be between 1 and 25 mJ/cm$^2$. For specific disinfection of viruses, the controlled UV dose should be between 38 and 187 mJ/cm$^2$.

The cradle holds the one BGM (or more than one BGM) through a receptacle configuration to accept a BGM. At least one advantage and consumer need being addressed by the present disclosure, among other things, includes disinfecting target areas most likely to come in contact with a patient and get contaminated with blood spatter or other bodily fluids.

The present disclosure alleviates at least several disadvantages of known methods for disinfecting devices by providing ultraviolet LEDs (UV LEDs) that disinfect using high intensity ultraviolet energy on the cradle, BGMs or both. It is possible that the cradle could be structured to include at least one chamber to fully enclose one (or more) BGM either fully or partially, so as to disinfect all or partial surfaces of the BGM. It is contemplated that one chamber hold a single BGM or multiple BGMs, or several chambers may hold a single BGM. In such a structure, there could be incorporated a door(s) or cover(s) to the chamber for the BGM to pass therethrough. Further, the chamber could include reflective type material including, but not limited to, one or more mirrors placed on the door or cover and or walls of the chamber either fully or partially to allow the UV rays to be reflected back into the chamber and on the BGM, so as to further intensify the disinfecting energy UV rays (or like light energy) on the BGM surfaces. The UV ray light can be pulsed or not pulsed, wherein the disinfecting energy intensity and duty cycle of the U.V-C exposure is based upon a plurality of BGM disinfection profiles, all defined by the duration.

Some embodiments provide a disinfection cradle which can be used for additional purposes, such as establishing bidirectional communication between a BGM and a computer or a network and/or supplying energy (power) to the BGM (i.e. for the purpose of recharging BGM battery). In general, bidirectional communication is required for component handshaking, data framing, and other communications between the BMG and the computer or network. In some embodiments, bidirectional communication between the cradle and the computer or network that the BGM is connected to allows for tracking which devices were disinfected as a means of logging the disinfection for health care establishment purposes. The logging may include generating, monitoring and updating the disinfection history of the diagnostic apparatus. In some embodiments, where the cradle is used for multiple diagnostic apparatuses, the cradle may be configured to track data for each device separately, to provide information when each apparatus was disinfected. In some embodiments, a timer or intensity tracker (or tracking function) for the disinfecting cycle is included as part of the bidirectional communication and data logging for the BGM, the tracker being configured to indicate when disinfecting is complete, or to measure the amount of disinfecting that was completed if the device was removed from the cradle before disinfection was complete. In some embodiments, the device will further comprise a lock out function that will lock the device from use if it hasn't been through a disinfecting cycle in a pre-selected period of time. In some embodiments, the lock out function further comprises a programmable feature allowing the lock out to be activated only after a pre-determined number of uses of the device without a disinfection procedure. It is possible that some embodiments may provide UV LEDs within the BGM itself in close proximity to the test strip port. Further, some embodiments may provide UV LEDs within an enclosure in which the BGM is placed, wherein the enclosure is closed with a door/cover.

FIG. 1 illustrates a front view of a disinfective cradle 22 and a blood glucose meter (BGM) 16 not inserted into the disinfective cradle, according to an embodiment. The BGM 16 is structured to be inserted into the disinfective cradle 22, wherein the disinfective cradle 22 is structured to accept the BGM 16 for the purpose of disinfecting one or more of the BGM surfaces in the immediate vicinity of its strip port. Further, the BGM 16 can be partly inserted in the cradle, thus subjecting the BGM 16 to a partial disinfection targeted at the surfaces most likely to be contaminated; in other embodiments, the BGM could be completely inserted in the cradle to disinfect all its surfaces. In some embodiments, the cradle 22 may include a receptacle in its top surface into which the BGM may be inserted.

FIG. 2 illustrates a front view of a disinfective cradle 22 and a BGM 16 inserted into the disinfective cradle 22. It is contemplated that in some embodiments regarding the shape of the disinfective cradle 22 can be structured and designed to accept the BGM 16, so as to hold the BGM 16 in an approximate up right position, laying down position with the rear of the BGM 16 facing downward or a side position of the BGM 16.

FIG. 3 illustrates a rear view of a disinfective cradle 22 and a BGM 16 inserted into the disinfective cradle 22. FIGS. 1-3 show the disinfective cradle 22 capable of disinfecting BGM 16. The disinfective cradle 22 includes a flat base, to allow for positioning on a surface. The disinfective cradle 22 also includes a receptacle located substantially on top of the disinfective cradle 22 into which a BGM may be rested for connection to the cradle. As shown in FIG. 3, the disinfective cradle 22 may include one or more ports that may be used to enable the cradle to communicate with auxiliary devices, to be recharged or both.

FIG. 4 is a perspective view of a disinfective cradle 22 according to an embodiment. In some embodiments, a BGM can be inserted into a receptacle in the cradle for the purpose of disinfecting one or more of the BGM's surfaces. FIG. 4 shows the disinfective cradle 22 having one or more light sources 4 positioned within a cavity or receptacle which can expose the BGM strip port on the BGM to UV light for disinfecting. It is possible that one or more light sources 4 may be positioned other than in the cavity or receptacle.

In some embodiments, ultraviolet LEDs (UV LEDs) can be used to deliver a controlled dose of ultraviolet light. In some embodiments, the cradle uses UV LEDs operating in a wavelength range between 100 nm to 280 nm which is at an operating wavelength range that can be effective for killing bacteria, molds and viruses. It can be appreciated that the UV LEDs can be pulsed ON and OFF at a certain duty cycle that reduces average power consumption but provides the benefit of very high intensity pulses of UV light, resulting in greater sanitization power. Alternatively, the LEDs can be continuously ON, or a combination of both continuous and pulse modes. Further, at least one advantage, among many, is that the cradle uses U.V-C LED technology because U.V-C LED's are compact, efficient, and produce limited heat and can be turned-ON and OFF very rapidly. It is contemplated the cradle may use alternative U.V-C sources such as U.V-C lamp(s), bulb(s), and tube(s) of a wavelength suitable for disinfection (within the 100 nm to 280 nm range).

Still referring to FIG. 4, UV LED light sources 4 can be comprised of one or more UV LEDs and one or more UV lens. According to some embodiments, the mechanical design of the cradle can be structured to maximize the amount of UV energy exposure toward the BGM strip port area (UV light reflectors) while minimizing any stray UV light escaping from the cradle/BGM mated pair (UV light shield) of the BGM. It is possible a UV lens can incorporate standard light pipe design principles and practices regarding geometry and surface finish to maximize the amount of UV light transmitted to the BGM strip port area. Light pipe design may be specifically based on the geometric shape of the device and the cradle, along with which areas of UV radiation is desired. For certain areas of the device and cradle it may be desirable to have higher level of UV concentration than other areas. However, unlike standard light pipes made of polycarbonate (which attenuates UV in the frequency of interest), the UV lens should be made of materials which allow the transmission of UV light such as UV transmissible Acrylic.

The cradle receptacle forming the receiving area for the BGM can be made of one or more materials. For example, it is possible at least one material can be a metallic UV-reflective surface type material so that any light emanating from the UV LED's is reflected toward the BGM to further intensify the UV energy and to concentrate the light produced by U.V-C sources toward the BGM target surfaces. In some embodiments, the receptacle of the cradle can be produced by metal stamping a thin sheet of polished stainless steel which also provides compatibility with chemical disinfectants normally found in Point of Care settings. Another possible type of material can include a UV-enhanced aluminum with a reflectivity of up to 85% @ 250 nm.

As noted above, the UV ray light can be pulsed or not pulsed, wherein the disinfecting energy intensity and duty cycle of the U.V-C exposure is based upon a plurality of BGM disinfection profiles, all defined by the duration. For example, the cradle 22 can automatically select an appropriate disinfection profile based on parameters received from a particular BGM and/or the device/network it is connected to, according to some embodiments. For example, if a cradle is designed to disinfect several models (or types) of BGMs, the cradle may detect the specific type of BGM being subjected to a disinfection cycle and then adjust the operating parameters accordingly, such as, by non-limiting example, the disinfection profile: duration of cycle, intensity and location of U.V-C sources. It is also possible the cradle or BGM may be equipped with a counter to maintain a record count of the disinfection cycles performed on a specific BGM, wherein the time between the last disinfection cycle, as well as the number of blood glucose readings taken since the last disinfection cycle, can trigger different UV disinfection profiles of different intensities/duration. The counter may also be used to establish a disinfection history for the specific BGM which may be communicated to a health care establishment.

Most microorganisms absorb UV at or near 260 nm, with viruses appearing to absorb quite a bit more at 240 nm or below. The disinfection cycle may concentrate disinfecting UV light utilized between about 220 nm and about 300 nm, preferably in a two-phased profile with one phase between about 220 nm and about 250 nm and a second phase between about 250 nm and about 280 nm, more preferably with one phase between about 225 nm and about 245 nm and a second phase between about 255 nm and about 275 nm, and more preferably with one phase at about 240 nm and a second phase at about 260 nm.

Still referring to FIG. 4, while, in some embodiments, the cradle 22 may be used solely for the purpose of disinfecting BGMs, in other embodiments, the cradle can be used for additional purposes. By way of non-limiting examples, the cradle 22 can be used to establish bidirectional communication between the BGM and another device such as, by non-limiting example, a computer or a network, and/or supplying energy (power) to the BGM (i.e. for the purpose of recharging BGM battery). It is noted that the cradle may be powered from a DC wall power-supply. Further, it is possible the disinfective cradle 22 can communicate with the BGM wirelessly or via electrical contacts 12. Thus, the cradle 22 can communicate with the BGM and/or supply energy to the BGM while a disinfection cycle is ongoing.

The BGM is equipped with a wired or wireless communication port (i.e. serial interface, infrared interface), to allow for example, the transfer of test results to a computer. Diabetes Management Software (DMS) may reside on the computer and can be used to manage the generated test results from the BMG. For example Nipro Diagnostics offers a DMS product designated as "True Manager". Communication port 8 provides power to the disinfective cradle 22. Communication port 8 can also be a USB connection port (thus providing 5 VDC to the cradle), among other things, or some other external power source can be used to power the cradle 22 such as a wall plug-in transformer or network (i.e. Ethernet). However, as noted above, the cradle may be powered from a DC wall power-supply. Further, the communication port 8 can also be used to allow the disinfective cradle 22, and the BGM received in the cradle, to communicate with external computing devices or other type of electronic devices.

Still referring to FIG. 4, the cradle may be equipped with a unique electronic I.D that it can communicate to the BGM and/or the device or network it is connected to, for the purposes of, for example, security advantages, authentication purposes or the like. For example, when communicating with the BGM, the cradle may transmit, among other things, its unique ID, or signals confirming the start and/or completion of a disinfection cycle. It is also possible that when communicating with a cradle, a BGM may transmit, among other things, its type (model) and serial number, whether or not it was used for blood glucose testing since its last disinfection. Further, it is contemplated that when communicating with an external device or network, the cradle can transmit data such as its unique ID, the status of its disinfection counter, the model and S/N of BGMs it disinfected along with date and time stamp of such events. Specifically, the BGM can store U.V-C disinfection events according to date and time-stamp in their memory and other related information.

Figure 5:
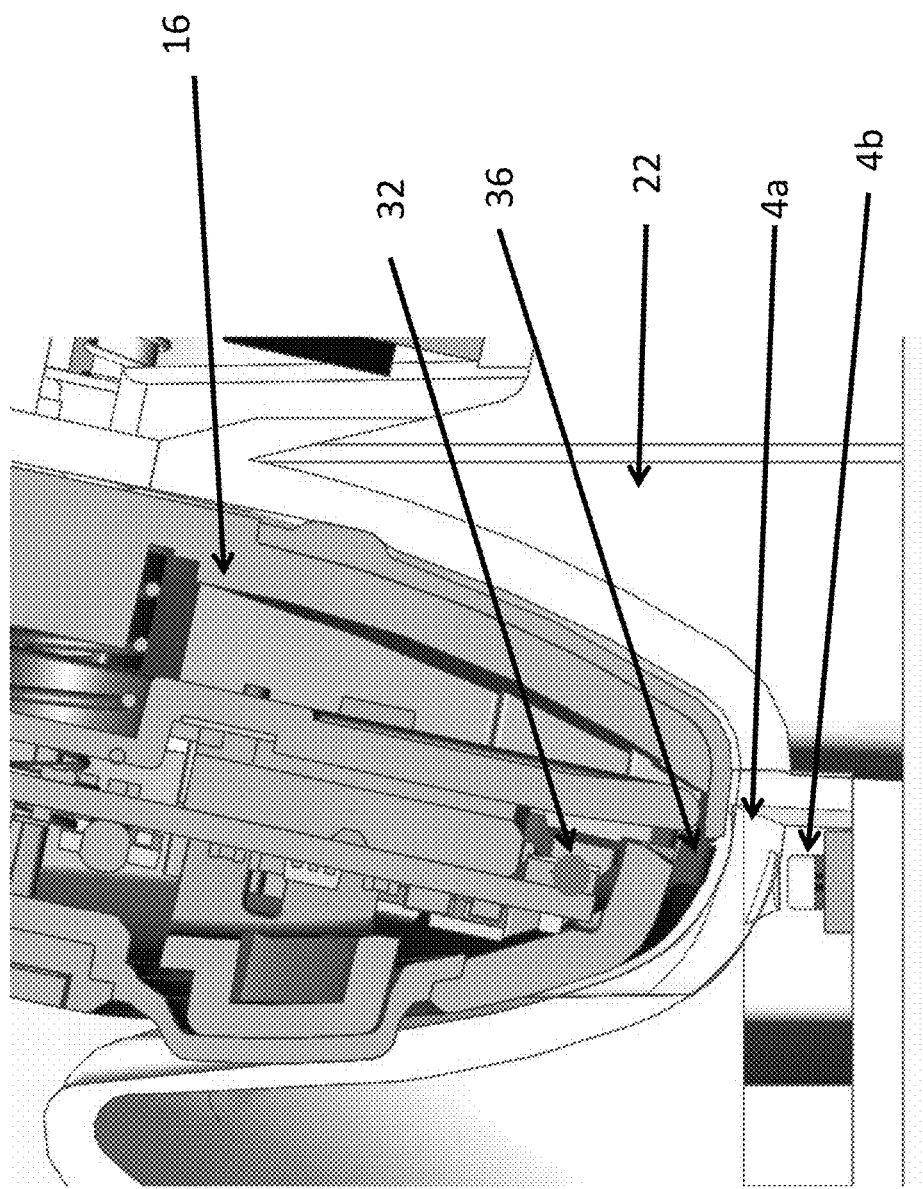
FIG. 5 is a cross section view of a disinfective cradle holding a blood glucose meter, according to some embodiments.

FIG. 5 is a cross section view of a disinfection cradle 22 holding a BGM 16 according to some embodiments. The disinfection cradle 22 can be equipped with UV LEDs 4*b* and UV lens 4*a* which deliver a controlled dose of ultraviolet light in a manner previously described. Additionally, UV LEDs 32 may be incorporated within the BGM 16 immediately inside of the strip port 36, or within other locations. The UV LED(s) are placed within the BGM housing so that direct UV light from these LED(s) reaches all or most of the surfaces in direct contact with a test strip. In some embodiments, the UV LEDs 4*b* are active when the test strip is not inserted. Alternatively, in some embodiments the lens 4*a* can direct UV light away from any sensitive area of the test strip (namely the chemistry area) when the test strip is inserted, including the electrical contacts interfacing with the strip. Placing UV LEDs 32 within the BGM 16 can help disinfect bio-burden in locations beyond the reach of the conventional wet-towel cleaners, since the action of these cleaners is limited to the exterior surfaces of the BGM. In some embodiments, power to the UV LEDs 32 is provided via the BGM cradle contacts in a manner completely independent from the BGM's battery power source. At least some embodiments incorporate a mechanical design of the cradle such that it maximizes the amount of U.V-C energy exposure of the BGM strip port area (reflectors, concentrators) while minimizing any stray U.V-C light escaping from the cradle/BGM mated pair (U.V-C light shield).

Figure 6:
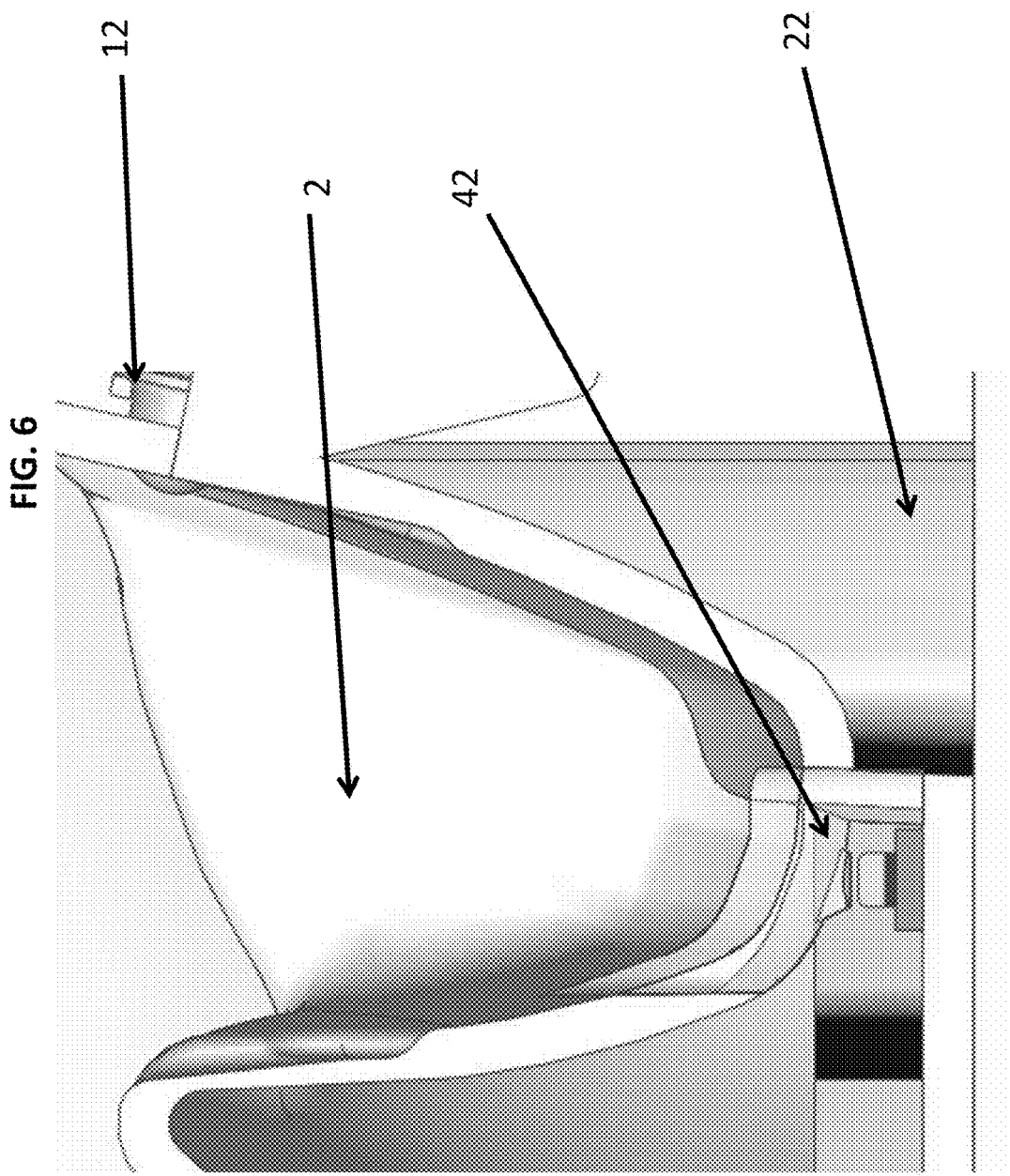
FIG. 6 is a cross section view of a disinfective cradle, according to some embodiments.

FIG. 6 is a cross section view of a disinfective cradle 22 in accordance with an embodiment of the present disclosure. The cradle 22 may house UV LED's behind a UV window 42, which can be comprised of polymer or glass or any other materials known to be transparent to UV wavelength. Thus, UV window 42 acts as a light-pipe to properly focus the UV radiation on the intended target regions. The shape of the window will be dependent on the shape of the cradle, the device and the LED placement. The disinfecting cradle 22 can communicate with a BGM via electrical contacts 12. The contacts 12 on the meter and the cradle 22 will provide an electrical connection between the cradle 22 and the BGM. The electrical connection allows for a communications connection between the cradle 22 and the BGM for serial, USB, network or other type of communication. Sealed connectors will be the best to avoid contamination getting into the cradle or into the device.

According to some embodiments, surfaces within the housing of disinfecting cradle 22 are designed in order to reflect UV exposure near areas of possible contamination (such as the strip port opening). In some embodiments, the cradle' UV LEDs illuminate the strip port region directly without a UV window.

Still referring to FIG. 6, according to at least some embodiments, the placement of the BGM 16 into the cradle 22 initiates the start of a disinfection cycle (U.V-C LED(s) turned-ON). Further, it is possible that the partial removal of the BGM 16 from the cradle 22 can be enough to abort a disinfection cycle (U.V-C LED(s) turned-OFF) in order to limit the exposure of users to stray U.V-C light. In some embodiments, the cradle 22 and BGM 16 are designed in such a manner that only the introduction of a legitimate BGM 16 can initiate the U.V disinfection process, wherein the cradle 22 verifies the presence of a legitimate BGM 16 using wired or wireless communication with a meter in the BGM 16. In some embodiments, the cradle 22 has a contact that touches a contact located on the back of the BGM 16 when the BMG 16 is inserted into the cradle 22, making an electrical contact between the cradle 22 and the BGM 16. This electrical contact sends an interrupt signal to the meter so the meter wakes up. When the meter wakes up, it sends out a serial data stream saying that it is awake. Software connected to the cradle 22 then knows the meter is inserted into the cradle 22 and ready to communicate, which verifies the presence of the legitimate BGM 16. When the meter is inserted into the cradle 22, the cradle 22 can wake up the meter via a communications port 8. The cradle 22 can send meter data over the communications port 8 to identify itself, at which time the meter can respond. If the response is acceptable by the cradle 22, the cradle 22 can turn on the disinfection cycle. If an invalid response is received by the cradle 22, the disinfection cycle will not be turned on. This lock out function will prevent someone accidentally putting something into the cradle 22 and have the UV radiation emit unintentionally. Therefore, only the proper device inserted will trigger a UV disinfection cycle. In additional embodiments, authentication methods could be via serial communication (as example above), RF communications like Bluetooth, RFID tag, mechanically keyed to have a specific fit inside cradle. In some embodiments the cradle 22 further comprises a mechanical switch that activates inside the cradle 22 only when the meter is fully inserted into the cradle 22, and is instantly deactivated when the meter is removed from the cradle 22.

Still referring to FIG. 6, the cradle or BGM may be equipped with a visual indicator (i.e. blue light for example) confirming that a disinfection cycle is underway. The cradle or BGM may also be equipped with an audio indicator (i.e. piezo beeper) signaling the completion of a disinfection cycle, or an unsafe condition (i.e. U.V-C light ON without BGM present) or possibly the start of a disinfection cycle.

The cradle 22 may be equipped with a counter to maintain a cumulative count of the disinfection cycles performed. Wherein when this feature exists, the cradle 22 may communicate this total count to the BGM 16 and/or any device or network the cradle 22 is connected to.

Figure 7:
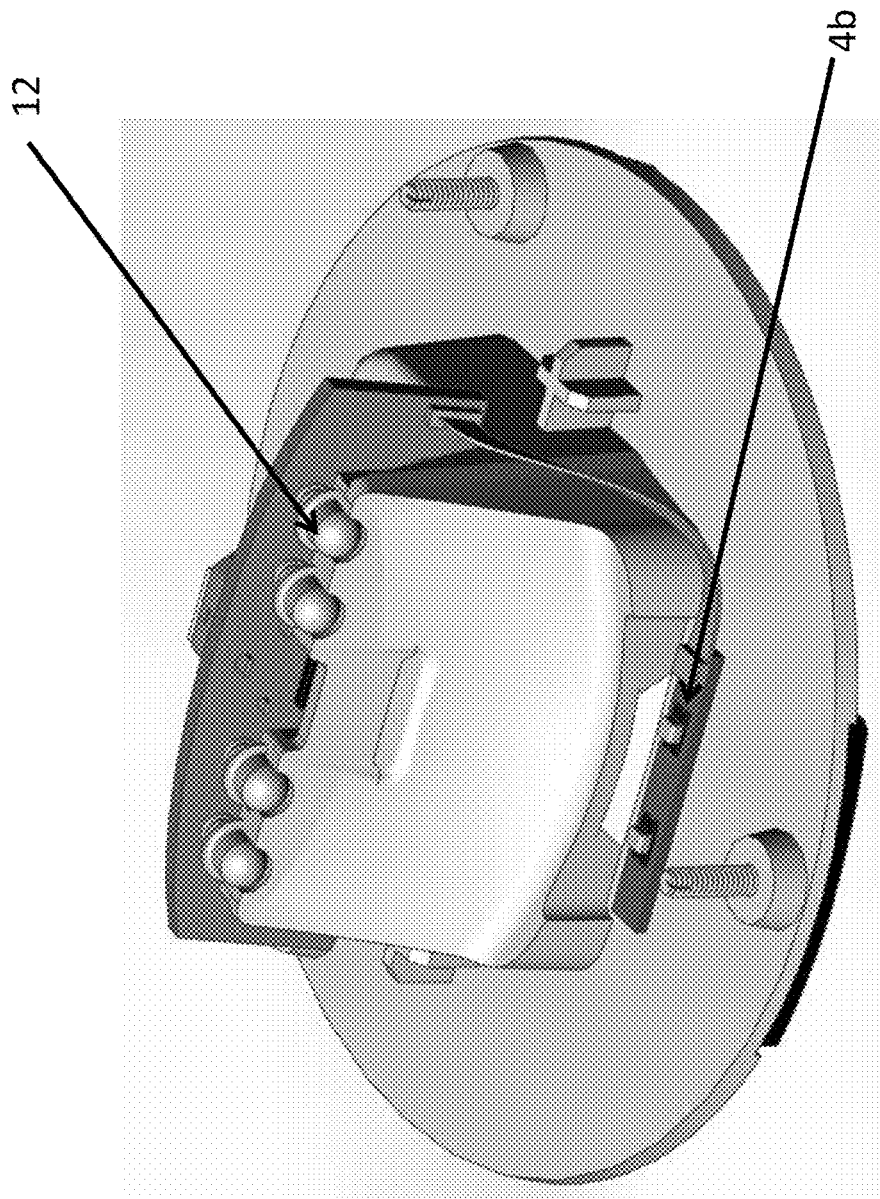
FIG. 7 is a perspective view of a disinfective cradle with the cover removed, according to some embodiments.

FIG. 7 is a perspective section view of a disinfective cradle with the cradle cover removed in accordance with an embodiment of the present disclosure. Electrical contacts 12 can provide power and communication to a BGM. UV LEDs 4b can deliver a controlled dose of ultraviolet light in a manner previously described. The cradle electronics controls the current of each LED 4b and as well as their duty cycle (ON/OFF/Pulsed), among other things.

In some embodiments, the BGM is fully inserted into the cradle. Fully inserting the complete length of the BGM into the cradle makes it possible to disinfect all of the BGM's surfaces approximate the test strip insertion area. In an alternative embodiment, the BGM is only partly inserted in the cradle, thus subjecting the BGM to a partial disinfection targeted at the surfaces most likely to be contaminated.

An alternative embodiment to a cradle is an enclosure in which the BGM is placed, the enclosure or chamber could be closed with a door/cover. It is noted that door or cover could have reflective type material attached to further intensify the UV light. The benefit of such embodiment is to expose all surfaces of the BGM to U.V-C light (U.V-C light complete immersion). As noted above, the chamber could house one or more BGMs.

In some embodiments, the cradle's UV LEDs can be automatically turned on upon the introduction of the BGM in the cradle, and automatically turned off after a pre-established period of time. By turning off the cradle's UV LEDs as soon as the removal of the BGM from its cradle is detected, the risk for a user to be exposed to UV radiation is significantly decreased.

The placement of the BGM into the cradle can initiate an immediate or delayed start of a disinfection cycle. As noted above, the cradle can be designed to disinfect several models (types) of BGMs, the cradle may detect the specific type of BGM being subjected to a disinfection cycle and adjust operating parameters accordingly (disinfection profile: duration of cycle, intensity and location of U.V-C sources).

In an alternative embodiment, BGMs may be equipped with U.V-C disinfection LED(s) in the immediate vicinity of their strip port opening or any other location within their housing. These BGM LEDs can be powered and controlled directly by the disinfection cradle, independently from the BGM battery. The BGM internal disinfection may precede, follow or be carried-out concurrently with the disinfection produced by the cradle UV light(s). Specifically, the UV LED-equipped BGM components within the housing are designed in order to concentrate the UV exposure near areas of possible contamination (such as the strip port opening), according to some embodiments.

Referring to FIG. 8, in some embodiments, a method of disinfecting a diagnostic apparatus which may include the steps of placing 10 the diagnostic apparatus in the cradle, administering 20 a disinfection cycle to the diagnostics apparatus, establishing 30 bidirectional communication between the diagnostic apparatus and a computer or a network, and communicating 40 a unique I.D. associated with the diagnostic apparatus or the cradle to the computer or the network. In some embodiments of the method, the cradle comprises a base having a receptacle configured to receive the diagnostic apparatus, and a UV LED source positioned in the receptacle configured to administer a disinfection cycle to the diagnostic apparatus by directing UV light outward at the diagnostic apparatus received in the receptacle. In some embodiments, the disinfection cycle comprises delivering a controlled UV dose from the UV LED source to a target area on the diagnostic apparatus. The controlled dose may be from about 1 mJ/cm$^2$ to about 200 mJ/cm$^2$. For specific disinfection of bacteria, the controlled dose may be set from about 1 mJ/cm$^2$ to about 25 mJ/cm$^2$. For specific disinfection of viruses, the controlled UV dose may set from about 38 mJ/cm$^2$ to about 187 mJ/cm$^2$. In some embodiments of the method, the computer or the network is part of a health care establishment such that the bidirectional communication allows the health care establishment to track a disinfection history of the diagnostic apparatus. The method of claim 17, wherein the cradle further comprises a unique electronic I.D. that may be communicated to the diagnostics apparatus and/or the computer or the network that is connected to the diagnostics apparatus.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A disinfection cradle for disinfecting a diagnostic apparatus, the disinfection cradle comprising:
   a base having a flat bottom surface for positioning the cradle on a surface;
   a receptacle disposed on a top surface of the cradle which receives a bottom portion of the diagnostic apparatus, wherein the diagnostic apparatus comprises a housing and a test strip port on the bottom portion of the diagnostic apparatus in the housing, wherein a size and shape of the receptacle approximate a size and shape of a bottom portion of the housing;
   a UV LED positioned in the receptacle such that when the diagnostic apparatus is received in the receptacle, the UV LED is in an alignment with the test strip port of the diagnostic apparatus to administer a disinfection cycle to the test strip port of the diagnostic apparatus; and
   a transparent window positioned between the UV LED and the test strip port when the diagnostic apparatus is positioned in the receptacle and configured to act as a light pipe to focus UV radiation from the UV LED positioned behind the transparent window to the test strip port of the diagnostic apparatus.

2. The disinfection cradle of claim 1, wherein the diagnostic apparatus is a blood glucose meter.

3. The disinfection cradle of claim 1, wherein the receptacle contains electrical contacts which provide power to the diagnostic apparatus.

4. The disinfection cradle of claim 1, wherein the diagnostic apparatus is in bidirectional communication with a computer or a network, such that the bidirectional communication allows a health care establishment to generate and monitor a record of a disinfection history of the diagnostic apparatus.

5. The disinfection cradle of claim 1, further comprising a tracking function configured to monitor the disinfection cycle and to indicate the degree of completion of the disinfection cycle.

6. The disinfection cradle of claim 1, further comprising one or more ports that enable the cradle to communicate with the diagnostic apparatus and one or more ports that enable the cradle to establish communication between the diagnostic apparatus and a computer or a network.

7. The disinfection cradle of claim 1, wherein the diagnostic apparatus further comprises a lock out function, wherein the lock out function prevents the diagnostic apparatus from functioning until the cradle has administered the disinfection cycle to the diagnostic apparatus.

* * * * *